(12) United States Patent
Yan et al.

(10) Patent No.: US 12,169,885 B2
(45) Date of Patent: Dec. 17, 2024

(54) COMPUTER PROCESSING TECHNIQUES FOR STREAK REDUCTION IN COMPUTED TOMOGRAPHY IMAGES

(71) Applicant: GE Precision Healthcare LLC, Wauwatosa, WI (US)

(72) Inventors: Ming Yan, Harland, WI (US); Jiahua Fan, New Berlin, WI (US); Zhye Yin, Niskayuna, NY (US)

(73) Assignee: GE Precision Healthcare LLC, Waukesha, WI (US)

( * ) Notice: Subject to any disclaimer, the term of this patent is extended or adjusted under 35 U.S.C. 154(b) by 357 days.

(21) Appl. No.: 17/652,507

(22) Filed: Feb. 25, 2022

(65) Prior Publication Data
US 2023/0274475 A1 Aug. 31, 2023

(51) Int. Cl.
*G06T 11/00* (2006.01)
*A61B 6/00* (2024.01)
*A61B 6/03* (2006.01)

(52) U.S. Cl.
CPC ............ *G06T 11/008* (2013.01); *A61B 6/032* (2013.01); *A61B 6/5205* (2013.01); *A61B 6/5258* (2013.01); *G06T 2211/441* (2023.08)

(58) Field of Classification Search
CPC . G06T 11/008; G06T 2211/441; A61B 6/032; A61B 6/5258; A61B 6/5205
See application file for complete search history.

(56) References Cited

U.S. PATENT DOCUMENTS

| | | | | | |
|---|---|---|---|---|---|
| 4,333,145 | A | * | 6/1982 | Heuscher | A61B 6/483 250/362 |
| 5,561,695 | A | * | 10/1996 | Hu | G01N 23/046 378/15 |
| 5,680,426 | A | * | 10/1997 | Ching-Ming | G06T 11/005 378/8 |

(Continued)

OTHER PUBLICATIONS

Wang, H et al. | "Personalized low dose CT via variable kVp", Proc. SPIE 9412, Medical Imaging 2015: Physics of Medical Imaging, 94122X (Mar. 18, 2015); https://doi.org/10.1117/12.2082353, 6 pages.

*Primary Examiner* — Amandeep Saini
*Assistant Examiner* — Daniella M. DiGuglielmo
(74) *Attorney, Agent, or Firm* — Amin, Turocy & Watson, LLP

(57) ABSTRACT

Computer processing techniques are described for reducing streaks in computed tomography (CT) images. According to an embodiment, computer-implemented method comprises obtaining, by a system comprising a processor, a pair of CT images reconstructed from a same set of projection data, the pair comprising a first image reconstructed from the projection data using a standard reconstruction process and a second image reconstructed from the projection data using a filtering reconstruction process that results in the second image comprising a first reduced level of streaks relative to the first image. The method further comprises generating, by the system, a third image by fusing a first subset of pixels extracted from one or more non-uniform areas in the first image and a second subset of pixels extracted from one or more uniform areas in the second image, wherein the third image comprises a second reduced level of streaks relative to the first image.

22 Claims, 12 Drawing Sheets

(56) References Cited

U.S. PATENT DOCUMENTS

| | | |
|---|---|---|
| 7,406,211 B2 | 7/2008 | Pena et al. |
| 7,558,362 B2 | 7/2009 | Shechter et al. |
| 10,249,066 B2 | 4/2019 | Zabic |
| 10,818,049 B2 | 10/2020 | Zabic |
| 2005/0094857 A1* | 5/2005 | Pena .................. G06T 5/70 |
| | | 382/130 |
| 2021/0042969 A1 | 2/2021 | Zabic |

* cited by examiner

COMPUTER PROCESSING TECHNIQUES FOR STREAK REDUCTION IN COMPUTED TOMOGRAPHY IMAGES

TECHNICAL FIELD

This application relates to medical image processing and more particularly to computer processing techniques for reducing streaks in computed tomography (CT) images.

BACKGROUND

Computed tomography (CT) has been one of the most successful imaging modalities and has facilitated countless image-based medical procedures since its invention decades ago. CT scanners use a rotating X-ray (XR) tube and a row of detectors placed in the gantry to measure XR attenuations by different tissues inside the body. The multiple XR measurements taken from different angles are then processed on a computer using reconstruction algorithms to produce tomographic (cross-sectional) images (reconstructed "slices") of the body. As the XR tube rotates around the body of the patient, the XR pathlength through the patient can be different at different tube locations. There is more XR attenuation when the XR pathlength is longer and thus less XR photons arrive at the detector for longer pathlengths relative to shorter pathlengths. This results in increased noise on XR signal projections with longer pathlengths compared to shorter pathlengths. The higher amounts of noise in the XR projections associated with longer pathlengths result in streaks in the reconstructed CT image.

One of the primary mechanisms for minimizing streaks attributed to longer pathlengths involve tube current modulation (TCM), wherein the tube current is increased for longer pathlengths and decreased for shorter pathlengths. However, TCM is limited by the hardware capacity of the CT scanner system at hand. Some CT scanners may not have the capability to adjust the tube current for different tube positions and/or may not have the capacity to increase the tube current high enough for longer pathlengths to obtain projections with sufficiently reduced noise to minimize corresponding streaks in the reconstructed images. In addition, increasing the tube current for longer pathlengths increases the amount of ionizing radiation exposure to the body, which can be harmful over time. Accordingly, techniques for minimizing streaks in CT images that do not suffer from these hardware restraints are needed.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are described that provide computer processing techniques for reducing streaks in computed tomography (CT) images.

According to an embodiment, a system is provided that comprises a memory that stores computer executable components, and a processor that executes the computer executable components stored in the memory. The computer executable components comprise an image processing component that obtains a pair of CT images reconstructed from a same set of projection data, the pair comprising a first image reconstructed from the projection data using a standard reconstruction process and a second image reconstructed from the projection data using a filtering reconstruction process that results in the second image comprising a first reduced level of streaks relative to the first image. The computer executable components further comprise a fusion component that generates a third image by fusing a first subset of pixels extracted from one or more non-uniform areas in the first image and a second subset of pixels extracted from one or more uniform areas in the second image, wherein the third image comprises a second reduced level of streaks relative to the first image. In one or more embodiments, the fusion component can determine noise level measures for each pixel of the second image and identify the first subset of pixels and the second subset of pixels based on the noise level measures and one or more defined threshold values for the noise level measures of the second subset.

In some embodiments, the standard reconstruction process comprises reconstructing the first image from the projection data without prefiltering the projection data and wherein the filtering reconstruction processes comprises filtering the projection data into prefiltered projection data and reconstructing the second image from the prefiltered projection data, wherein the prefiltered projection data comprises projections with reduced noise as function of pathlengths of the projections or function of a combination of the pathlengths and tube current, and wherein an amount of the reduced noise increases as the pathlengths increase or the tube current decreases. In some implementations of these embodiments, the (original) projection data can be obtained by the image processing component. In other embodiments, the original projection data may not be provided. With these embodiments, the computer executable components can further comprise a projection component that estimates the projection data from the first image using a forward image projection process, resulting in simulated projection data, and wherein the filtering reconstruction processes comprises filtering the simulated projection into the prefiltered projection data as opposed to the filtering the projection data. The computer executable components can further comprise a projection space filtering component that generates the prefiltered projection data from the projection data or the simulated projection data. To facilitate this end, the projection space filtering component estimates the pathlengths of the projections using a projection smoothing process, estimates noise levels of the projections based on the pathlengths or a combination of the pathlengths and tube current, and determines the amount of the reduced noise for the projections based on the noise levels. The computer executable components can further comprise a reconstruction component that generates the second image from the prefiltered projection data. The reconstruction component may also generate the first image from the (original) projection data.

In other embodiments, the filtering reconstruction process comprises an image space filtering processes that is used to generate the second image by filter processing the first image. With these embodiments, the computer executable components further comprise an image space filtering component that performs the image space filtering process on the first image to generate the second image.

In one or more additional embodiments, the computer executable components can further comprise a training component that receives a plurality of pairs of CT images respectively comprising original images generated using the standard reconstruction process and fused images corresponding to the third image generated by the fusion component. With these embodiments, the training component can train an image transformation model comprising a neural network to transform the original images into corresponding versions of the fused images, resulting in a trained image transformation model. The computer executable components can further comprise an inferencing component that receives a new CT image reconstructed from a new set of projection data using the standard reconstruction process and generates an optimized image with a reduced level of streaks relative to the new CT images using the trained image transformation model. In some implementations of these embodiments, the computer executable components further comprise a training data preparation component that determines streak data for each pair of the plurality of pairs based on differences between the original images and the fused images, and the training component trains the neural network to estimate the streak data given the original images as input, resulting in estimated streak data. With these implementations, the image transformation model can be configured to remove the estimated streak data from the original images to generate the corresponding versions of the fused images.

In some embodiments, elements described in the disclosed systems and methods can be embodied in different forms such as a computer-implemented method, a computer program product, or another form.

DETAILED DESCRIPTION

Figure 1:
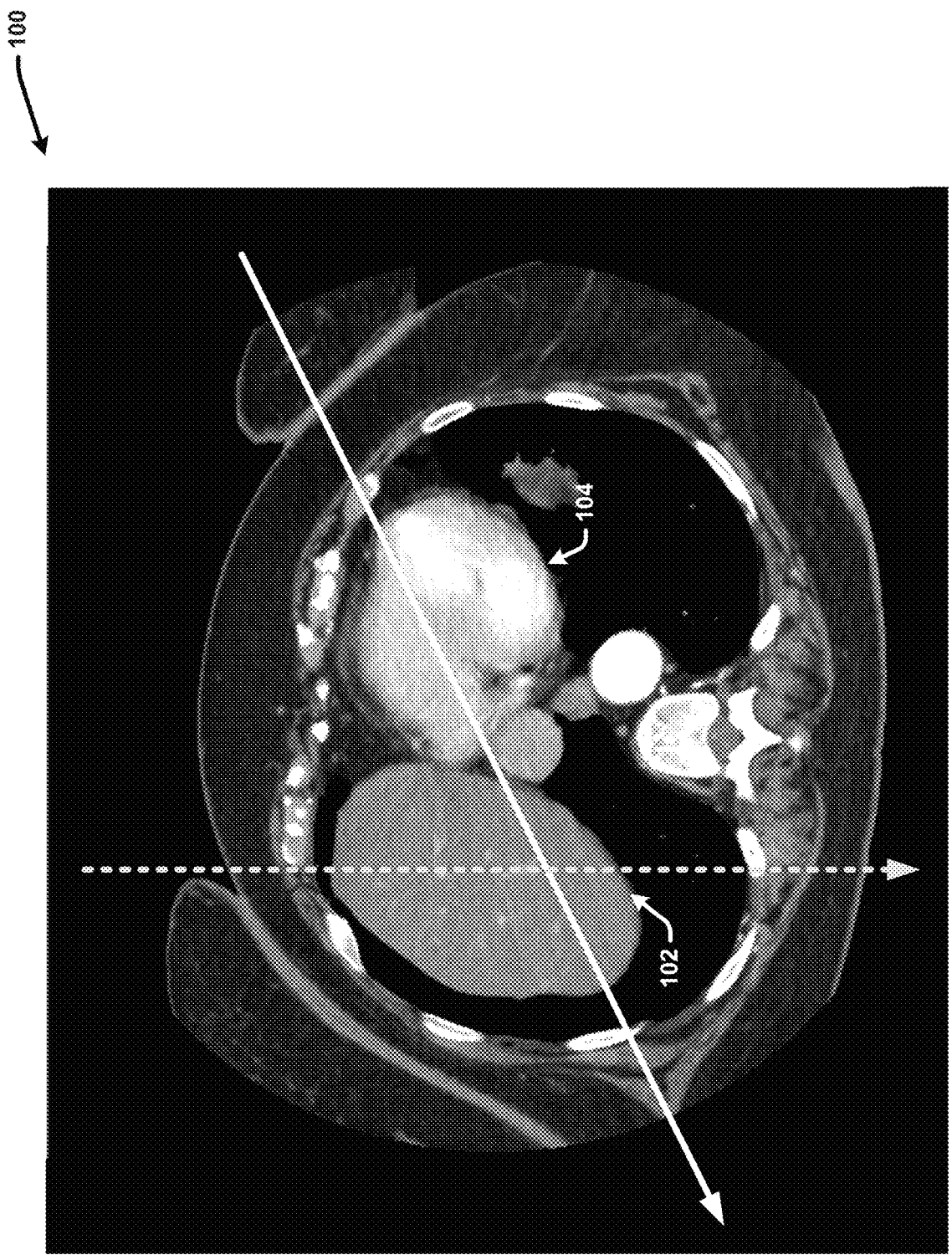
FIG. 1 illustrates pathlength-based streak generation in an example computed tomography (CT) image in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that provide computer processing techniques for reducing streaks in CT images. The disclosed techniques aim to reduce streaks in a CT image while maintaining spatial resolution and structure details in an image by adaptively blending selected pixels from two CT images reconstructed from the same set of original captured XR projection data in different manner. In this regard, one of the two images is generated from the original projection data using a standard CT image reconstruction procedure that results in the image comprising streaks in at least some areas associated with longer projection pathlengths. The other image is processed using a filtering reconstruction process that aims to suppress noise attributed to projections with longer pathlengths. The second image generated using the filtering reconstruction process has fewer streaks relative to the first image, yet some blurring or reduced resolution effects attributed to the noise reduction. Different filtering reconstruction processes are described herein for generating the second image.

The disclosed techniques further extract a first subset of pixels from the first image from non-uniform areas (e.g., areas where higher resolution pixels are needed for more detailed structures, such as areas associated with bones, organs, target tissues, etc.) and a second subset of pixels from the uninform areas in the second image. The disclosed techniques further employ an adaptive blending process that comprises fusing the first and second subsets of pixels to generate a third and final CT image (referred to herein as a fused or blended image) that has a reduced level of streaks relative to the first image in the uniform areas yet preserves the resolution of the first image in the non-uniform areas.

The disclosed subject matter further provides techniques for reducing streaks in CT images using principles of artificial intelligence (AI) and machine learning (ML). In this regard, in one or more additional embodiments, the methods for generating fused images described above can also be used to prepare a training data set for training a deep neural network model to generate an optimized image corresponding to the fused image described above given an original CT image (e.g., processed using a standard reconstruction processes) as input. The training dataset comprises pairs CT images, wherein each pair comprises an original CT image reconstructed using the standard reconstruction process (e.g., corresponding to the first image above) and a fused CT image corresponding to the third image described above generated using the adapted blending techniques disclosed herein. In some embodiments, the training process comprises training the neural network to transform the original CT images into corresponding versions of their paired fused images. Additionally, or alternatively, the training process can comprise training the neural network to estimate streak data included in the original CT images, wherein the streak data used for the training process can be calculated based on difference between the original CT images and their paired fused images. With these embodiments, the output of the trained neural network comprises predicted streak data for a given original CT image. After the network has been trained, the trained neural network can be applied to a new original CT image (e.g., with streaks) to generate estimated streak data for the new CT image. The disclosed techniques can further generate a final optimized image by removing the estimated streak data (output by the neural network model) from the original CT image.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates pathlength-based streak generation in an example computed tomography (CT) image 100 in accordance with one or more embodiments of the disclosed subject matter. The example CT image 100 illustrated in FIG. 1 is an axil cross-sectional image of a patient's abdomen depicting a view of the patient's liver 102 and heart 104. The CT image 100 is a standard CT image reconstructed using a conventional or standard CT image reconstruction process from original CT scan projection data captured using a conventional CT scanning procedure. In accordance with conventional CT scanning procedures, the patient is centered on a motorized scanning table through a circular opening in the CT imaging system. As the patient passes through the CT imaging system via the motorized scanning table (e.g., incrementally forward or backward to generate different tube positions relative to the body of the patient) an XR tube providing a source of XRs rotates around the inside of the circular opening. The XR tube produces a narrow, fan-shaped beam of XR used to irradiate a section of the patient's body. In typical examinations there are several phases; each made up of 10 to 50 rotations of the XR tube around the patient in coordination with the table moving through the circular opening. Detectors on the exit side of the patient record the XR signals exiting the section of the patient's body being irradiated as an XR "snapshot" at one position (angle or view) of the XR tube. More particularly, the CT scanner uses an XR tube that projects XR photons through the body of the patient and an array of detectors placed in the gantry on the opposite side of the body to measure XR attenuations of the photons by different tissues inside the body based on the amount of photons arriving at the detector cells. Thus, each "snapshot" corresponding to each tube position can comprise a plurality of projections. The number of projections obtained for each tube position (e.g., each tube angle or view) depends on configuration of the detector cells, which can include an array of one or more rows and columns of cells. Many different "snapshots" (angles) are collected during one complete (e.g., 360°) rotation. The collection of projections captured during the scanning process is then sent to a computer to reconstruct all of the individual "snapshots" into a cross-sectional image (slice) of the internal organs and tissues for each complete rotation of the XR tube. In this regard, for conventional (e.g., non-helical) CT scanning procedures, the collection of signals (referred to herein as projections) captured at each tube position (e.g., angle or view) for a single rotation are then back projected to create the reconstructed image corresponding to a cross-sectional slice of the body for that rotation.

As the XR tube rotates around the body of the patient, the XR pathlength between the tube and the detector can be different at different tube positions. There is more XR attenuation when the XR pathlength is longer and thus less XR photons arrive at the detector for longer pathlengths relative to shorter pathlengths. This results in increased noise on XR signal projections with longer pathlengths compared to shorter pathlengths. The higher amounts of noise in the XR projections associated with longer pathlengths result in streaks in the reconstructed CT image. For example, as illustrated in FIG. 1, the solid arrow line corresponds to a projection with a relatively long pathlength (e.g., the length between XR tube and the detector) and the dashed arrow line correspond to a projection with a shorter pathlength. The projection corresponding to the solid arrow line has higher noise relative to the projection along the dashed arrow line due to less photons arriving at the detector. As a result, streaks are present in the reconstructed CT image 100 along the solid arrow line.

The disclosed subject matter is directed to systems, computer-implemented methods, apparatus and/or computer program products that provide computer processing techniques for reducing such streaks in CT images attributed to longer pathlengths. The disclosed techniques aim to reduce streaks in a CT image while maintaining spatial resolution and structure details in an image by adaptively blending selected pixels from two CT images reconstructed from the same set of original captured XR projection data in different manner.

Figure 2:
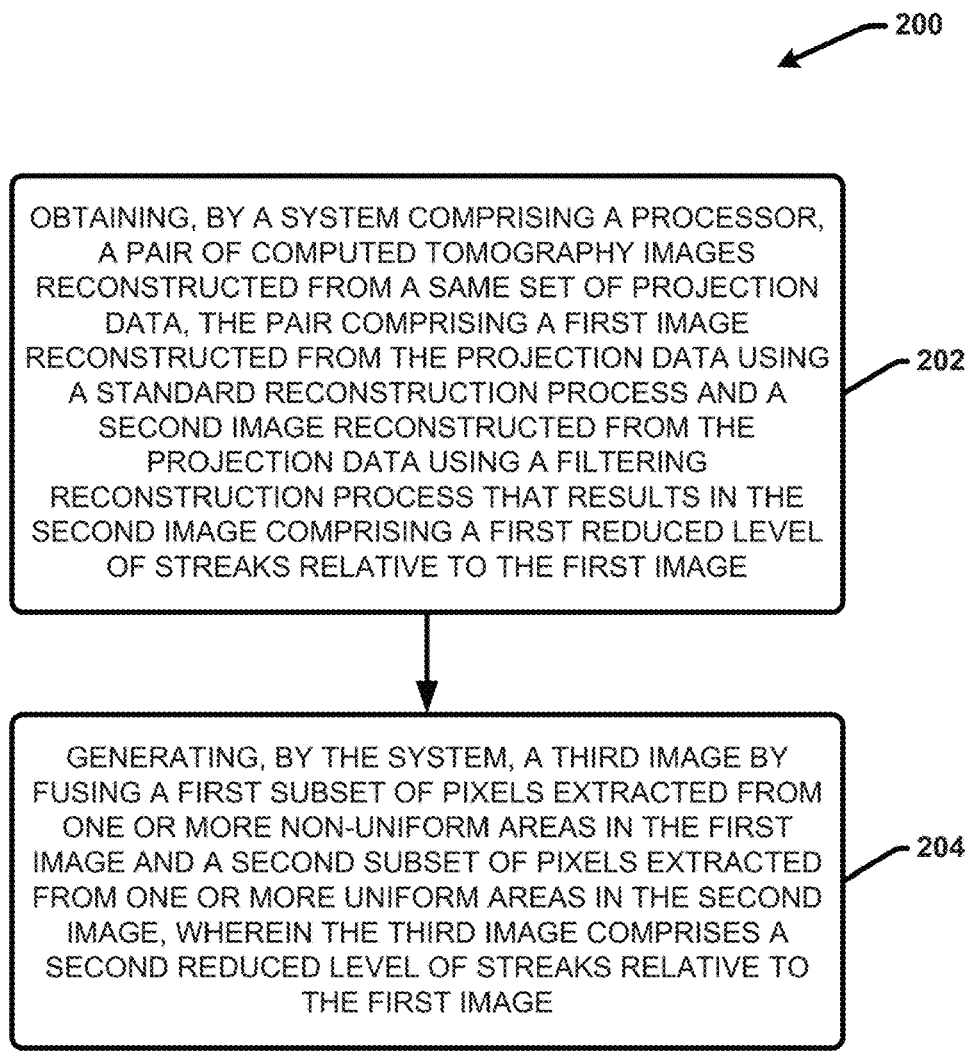
FIG. 2 presents a high-level flow diagram of an example computer-implemented process for reducing streaks in a CT image in accordance with one or more embodiments of the disclosed subject matter.

FIG. 2 presents a high-level flow diagram of an example computer-implemented process 200 for reducing streaks in a CT image in accordance with one or more embodiments of the disclosed subject matter. In accordance with process 200, at 202 a system comprising a processor, (e.g., system 300 and/or system 800 described infra), obtains a pair of CT images reconstructed from a same set of projection data, the pair comprising a first image reconstructed from the projection data using a standard reconstruction process and a second image reconstructed from the projection data using a filtering reconstruction process that results in the second image comprising a first reduced level of streaks relative to the first image. As described in great detail infra, in some embodiments, the system can receive or otherwise obtain the original projection data and perform the standard reconstruction process to generate the first image using the original projection data. The system can also perform the filtering reconstruction process using the original projection data to generate the second image. With these embodiments, the filtering reconstruction process can comprise a projection space filtering process that involves filtering the original projection data based on respective pathlengths associated with the projections to generate filtered projection data and reconstruct the second image from the filtered projection data. In other embodiments, the system may receive the first image as already reconstructed using the standard reconstruction process and perform the filtering reconstruction process starting from the first image to generate the second image. In some implementations of these embodiments, this can involve forward projecting the first image to obtain simulated projection data for the first image and performing the projection space filtering process using the simulated projection data. In other implementations, the system can employ a different filtering reconstruction process referred to as an image space filtering reconstruction process to generate the second image from the first image. These filtering reconstruction processes are described in greater detail infra.

At 204, process 200 further comprises generating, by the system, a third image by fusing a first subset of pixels extracted from one or more non-uniform areas in the first image and a second subset of pixels extracted from one or more uniform areas in the second image, wherein the third image comprises a second reduced level of streaks relative to the first image. In his regard, the system performs an adaptive blending process that involves blending one or more portions of the first image, the original CT image having a higher resolution yet streaks, with one or more portions of the second image, the filtered image with reduced noise and thus less streaks yet some blurring effect. As a result, the third image, referred to herein as the "fused image" or "blended image," has a reduced level of streaks relative to the first image in the uniform areas yet preserves the resolution of the first image in the non-uniform areas. The portions used from the first image can include those where higher resolution pixels are needed for more detailed structures, such as areas associated with bones, organs, target tissues, etc., while the portions used from the second image include those where lower resolution pixels are sufficient, such as those associated with uniform areas depicting less detailed anatomical structures. For example, with reference back to FIG. 1, the uniform areas in the example CT image 100 may correspond to the areas defined by the liver 102 and the heart 104 while the non-uniform areas may include the other anatomical structures excluding the liver 102 and the heart 104. Techniques for identifying and selecting the specific subsets of pixels to be extracted from the first image and the second image are described in detail infra.

Figure 3:
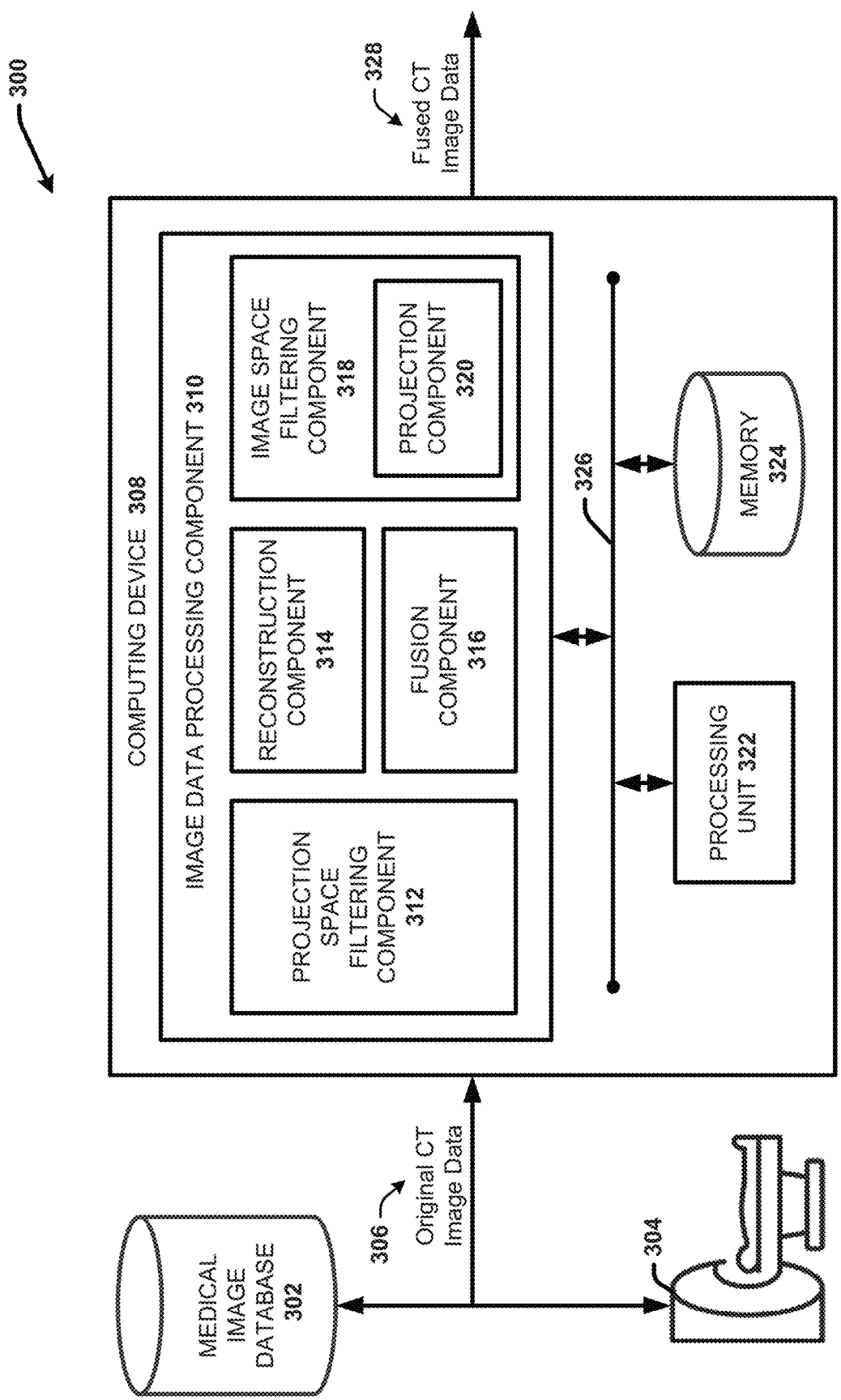
FIG. 3 presents an example computing system that facilitates reducing streaks in CT images in accordance with one or more embodiments of the disclosed subject matter.

FIG. 3 presents an example computing system 300 that facilitates reducing streaks in CT images in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

In this regard, computing system 300 provides an example computing system comprising a computing device 308 that includes machine-executable components configured to perform one or more of the operations described in process 200 and additional processes described herein. The computer executable components include an image data processing component 310 configured to receive and process original CT image data 306 into fused CT image data 328 using various computer executable sub-components, including projection space filtering component 312, reconstruction component 314, fusion component 316, image space filtering component 318 and projection component 320. These computer/machine executable components (and other described herein) can be stored in memory associated with the one or more machines. The memory can further be operatively coupled to at least one processor, such that the components can be executed by the at least one processor to perform the operations described. For example, in some embodiments, these computer/machine executable components can be stored in memory 324 of the computing device 308 which can be coupled to processing unit 322 for execution thereof. The computing device 308 further include a device bus 326 that communicatively and operatively couples image data processing component 310 and its sub-components (e.g., the projection space filtering component 312, the reconstruction component 314, the fusion component 316, the image space filtering component 318 and the projection component 320) to the processing unit 322 and the memory 324. Examples of said and memory 324 and processing unit 322 as well as other suitable computer or computing-based elements, can be found with reference to FIG. 12, and can be used in connection with implementing one or more of the systems or components shown and described in connection with FIG. 3 or other figures disclosed herein.

The original CT image data 306 can comprise original (raw or unprocessed) CT projection data captured via a CT scanner 304 in accordance with a CT scan of an anatomical region of a patient. The original CT image data 306 may also include one or more CT images reconstructed from the original CT projection data using a standard or conventional CT image reconstruction process (e.g., a reconstruction process other than the filtering reconstruction processes disclosed herein). In this regard, in some embodiments, the original CT image data 306 can comprise the projection data and/or the first image described with referenced to process 200 and the fused CT image data can correspond to the third image described with reference to process 200. In some embodiments, the image data processing component 310 can receive the original CT image data 306 directly from the CT scanner 304 and/or as stored in a medical image database 302. The computing device 308 can further be communicatively and operatively coupled to the CT scanner 304 and/or the medical image database 302 via one or more wired or wireless communication networks. In other embodiments, the original CT image data 306 may be stored locally in memory 324. In this regard, the deployment architecture of computing system 300 can vary. In some embodiments, the computing device 308 can correspond a single computing device (e.g., real or virtual). In other embodiments, the computing device 308 can correspond to two or more separate communicatively coupled computing devices operating in a distributed computing environment. Various alternative deployment architecture variations can also be used.

With reference to FIGS. 2 and 3, the projection space filtering component 312 can perform a projection space filtering process using the original CT image data 306 to generate filtered projection data. The reconstruction component 314 can further processes the filtered projection data to generate or reconstruct the second image described with reference to process 200. In implementations in which the original CT image data 306 does not include a previously reconstructed original CT image corresponding to the first image in process 200, the reconstruction component 314 can also perform a standard CT image reconstruction process using the original CT projection data (included in the original CT image data 306) to generate the first image. Additionally, or alternatively, the image space filtering component 318 can perform an image space filtering process using the original CT image data 306 to generate the second image described with reference to process 200. The fusion component 316 can further perform the adaptive blending of the first and second images to generate the fused CT image data 328 corresponding to the third image in process 200.

The projection space filtering process performed by the projection space filtering component 312 involves filtering an original set of projection data (e.g., native, as captured by the CT scanner 304) based on respective pathlengths (l) of the projections to remove noise associated with the respective projections, wherein the amount of noise removed increases as the pathlength increases. In this regard, the original set of projection data can comprise an original set or group of projection signals captured during a CT scan that is used to create a single two-dimensional (2D) image corresponding to a cross-sectional image of the patient's body. For example, as applied to conventional CT scanning, the set of projection data (P) can comprise the complete set of projections captured during a single rotation of the XR tube around the patient. It should be appreciated that the filtering process discussed herein can be applied filter multiple sets of projection data (P) captured during different entire rotations of the CT scanning procedure (e.g., all captured projection data at different tube rotations corresponding to different cross-sectional regions of the patient). The filtering processes discussed herein can also be applied to projection data captured in association with helical scanning and multi-slice scanning. With these embodiments the set of projection data (P) used to create a single 2D image can include projections associated with helical and partial rotations of the gantry.

Each set of projection data (P) comprises a plurality of subsets of projection data, one for each view or tube position/angle within the rotation. As noted above, the pathlength through the patient can vary for each view. Each subset of projection data can further be defined by a plurality of individual projections (p) corresponding to the signals received at individual detector cells of the detector used, which may be defined by one or more rows and one or more columns of detector cells (i.e., a detector array). In some implementations, the pathlength can also vary within a same view for each detector cell channel, wherein the channel corresponding to a specific column (col) and row (col, row). In this regard, each individual projection (p) included in the set of projection data (P) may be defined by a view, a detector column (col), and a detector row (row) as follows: p(col, row, view). At a high level, the projection space filtering processes comprises filtering the set of projection data P to create filtered projections $p_f$ with similar noise levels (e.g., within a defined degree of deviation) for each view as a function of the pathlength associated with each projection p, wherein the pathlength (l) can vary per view and detector cell row and column, and wherein the amount of noise filtered out of the projections p using the filtering function F increases as the path length increases. The pathlength (l) for each detector cell and view is estimated (as described in greater detail below). In other words, the projections p are filtered using a filtering function F to reduce or remove the noise on the projections with longer pathlengths to be similar (e.g., relative to a defined degree of deviation) to the noise on the projections with shorter pathlengths. Expressed mathematically, in some embodiments, the filtered projections pf can be defined by Equation 1 below:

$$p_f(\text{col},\text{row},\text{view})=F(p(\text{col},\text{row},\text{view}),\text{pathlength}(\text{col},\text{row},\text{view})) \quad \text{Equation 1.}$$

In some embodiments, the projection space filtering process can also filter the projection data as a function of a combination of the respective pathlengths of the projections and tube currents of the respective projections. The tube current is typically measured in milliampere-seconds, also more commonly known as mAs, and is a measure of radiation produced (milliamperage) over a set amount of time (seconds) via an x-ray tube. In this regard, some CT scanning systems are capable of adjusting the tube current the XR tube (i.e., the XR photon source) at different tube angles (e.g., views) and positions relative to the patient the course of a CT scan, a process known as tube current modulation. TCM may be used to increase the tube current (i.e., the number of x-ray photons) for longer pathlengths and thicker body regions and decrease the tube current for shorter pathlengths and thinner body regions. As patients are not homogeneous cylinders, the end result is typically that the tube current oscillates up and down within a single rotation of the gantry, and increases, on average, through thick body regions (e.g., the shoulders and hips), and decreases, on average, through thinner body regions (e.g., the chest). In this regard, the TCM can be adjusted to dynamically control the number of photons at every projection through the patient. As described in the Background section, increasing the tube current for longer pathlengths can increase the number of photons arriving at the detector cells and thus decrease the amount of corresponding noise in the projections to at least some degree. The TCM used thus significantly impacts radiation dose and corresponding image quality and can vary rapidly across multiple CT acquisition rotations as well as within a single rotation of the gantry. With these embodiments, the specific tube current mA used for each view can also be factored into the projection space filtering equation, in accordance with Equation 2 below:

$$p_f(\text{col},\text{row},\text{view})=F(p(\text{col},\text{row},\text{view}),\text{pathlength}(\text{col},\text{row},\text{view}),mA(\text{view})) \quad \text{Equation 2.}$$

In accordance with Equations 1 and 2 above and the image space filtering processes, the original set of projection data (P) can be provided with the with original CT image data 306. The original set of projection data P includes information defining the projection p values for each view, that is, each (p(col,row,view). In implementations in which different mAs are used for different views, the original projection data will also include the tube current mA values used for each view; mA(view). The projection space filtering processes performed by projection space filtering component 312 involves estimating the pathlengths for each projection p using a projection smoothing process, estimating the noise levels of the projections based on the pathlengths or a combination of the pathlengths and the tube current, determining amounts of the noise reduction (e.g., the F function values or filter strength) based on the noise levels, and generating the prefiltered projections ($p_f$) by removing the amounts of reduced noise from the projections p in accordance with Equations 1 or 2 above. In this regard, the projection space filtering processes results in transformation of the original set of projection data P into a set of prefiltered projection data $P_f$ that comprises filtered projections $p_f$(col, row,view) for at least some (one or more) of the different views and/or channels. In this regard, it should be appreciated that in some implementations, original projections p associated with relatively short pathlengths may not be filtered.

Additional information regarding each of these steps of the projection space filtering processes are now described. In one or more embodiments, the projection space filtering process can initially involve a pre-smoothing process wherein the original projections p are pre-smoothed to reduce noise and to obtain an estimation of the pathlength l associated with each projection in accordance with Equation 3.

$$l(col, row, view) = \frac{p_s(col, row, view)}{\mu_w}. \quad \text{Equation 3}$$

In accordance with Equation 3, the projection space filtering component 312 can compute the pathlength l for each pre-smoothed projection $p_s$ defined by a specific view (i.e., angle/position of the XR tube), detector column, and detector row (i.e., (col,row,view)) using the wat attenuation coefficient and $\mu_w$ is the water attenuation coefficient. Since $\mu_w$ is a constant value, $p_s(col,row,view)/\mu_w$ can be used as an estimation of the pathlength l for each pre-smoothed projection $p_s(col,row,view)$.

Once the estimated pathlengths l for each pre-smoothed projection $p_s(col,row,view)$ have been determined, the projection space filtering component 312 can estimate the noise level σ(col,row,view) associated with each projection p(col,row,view) based on its pathlength. In one or more embodiments, this can be achieved using a sigmaestimate function and predetermined reference information for the CT imaging system from which the original projection data P was obtained that maps different pathlengths and tube current values mA to estimated noise levels. This predetermined reference information can be generated using phantom studies and stored in memory 324 (or another suitable memory storage) in the form of a look-up table. In particular, the noise level estimates are determined for each channel (e.g., each (col, row) cross views. To facilitate the reconstruction, a segment of projections can be used, and the starting view and end view is $V_s$ and $V_e$. The noise levels can be estimated based the pre-smoothed projection $p_s$ in accordance with Equation 4 or the pathlength l in accordance with Equation 5. To this end, lowest low noise level for channel (col, row) cross view $\sigma_{low}(col,row)$ is estimated.

$$\sigma(col,row,view)=sigmaestimate(p_s(col,row,view),mA) \quad \text{Equation 4}$$

$$\sigma(col,row,view)=sigmaestimate(l(col,row,view),mA) \quad \text{Equation 5.}$$

The sigmaestimate function in the former sub step can be pre-constructed for the CT imaging system using phantom studies. In particular, a phantom object can be scanned using the CT imaging system multiple times at for each mA setting of a plurality of different mA settings. For example, at a first mA setting, the phantom can be scanned multiple times to obtain multiple measurements for each path length p(l,i), wherein l is the path length and i∈[1 m] is the noise on level on path length l, which can be calculated with the standard deviation for std(p(l,i)) i∈[1 m]. After the noise level for each pathlength is acquired at this first mA, the same processes can be repeated at different mAs to obtain noise level measurement for each pathlength at different mAs.

After the noise levels are estimated for each pathlength and mA using the phantom, a look up-table can be formed which can be used to estimate the noise level a on projections p and/or the pre-smoothed projections $p_s$ based on their estimated pathlengths l. The tube output can also be factored into the equation and scaled based on air calibration data. In particular, the projection space filtering component 312 can calculate the estimated noise level $\sigma_p(col,row,view)$ for each projection p(col,row,view) with the sigmaestimate function formed using the phantom and the look-up table.

Once the noise levels are estimated for each projection, the projection space filtering component 312 can filter the projections with kernel K based on the lowest noise level for each channel and/or view to make all the projections associated with each channel and/or view have a noise level that is the same or substantially similar (e.g., within a defined degree of deviation) to the lowest noise level for that channel and/or view, (noting again that each view includes a subset of projections with different path lengths and noise levels). This means that for each channel and/or view, the noise of the corresponding filtered projections should be closest to the lowest noise level for that channel/view. This can be expressed mathematically as follows: filter the p(col,row,view) with kernel K to reduce estimated noise level $\sigma_p(col,row,view)$ to be close to $\sigma_{low}(col,row)$, in accordance with Equation 6, T is a predefined threshold parameter, and when $\sigma_p(col,row,view)$ is controlled under the predefined range T, streaks are largely reduced or not visible.

$$\sigma_p(col,row,view)/\sigma_{low}(col,row)<T \quad \text{Equation 6.}$$

In this regard, K corresponds to a convolutional kernel. The strength of the K used is directly proportional to the degree of the estimated noise. That is, when the noise associated with a projection is high, a stronger filtering kernel K is used, and vice versa.

The convolution kernel K is determined by the following method. The convolution kernel K is a m*n matrix, all elements are in K smaller or equal to 1. The sum of all elements in K is one. The center value of K is the largest value in K. the noise reduction ratio r can be calculated in accordance with Equation 7.

$$r = sqrt\left(\sum_{i=1,j=1}^{i=m,j=n} K(i,j)^2\right). \quad \text{Equation 7}$$

A projection p(col,row,view) with noise level σ(col,row,view) is convoluted with K, and the new noise level $\sigma_p(col,row,view)$ can be calculated using Equation 8.

$$\sigma_p(col,row,view)=r*\sigma(col,row,view) \quad \text{Equation 8.}$$

A set of K can be formed, and r can be pre calculated. In the former step, we require $\sigma_p(col,row,view)/\sigma_{low}(col,row)<T$, then a desired noise level after filtering is $\sigma_{low}(col,row)*T$ and the desired ratio r=σ(col,row,view)/$\sigma_{low}(col,row)*T$, with the r, we can find predefined kernel K and use K filter projection p(col,row,view).

As noted above, the projection space filtering processes results in transformation of the original set of projection data P into a set of prefiltered projection data $P_f$ that comprises filtered projections $p_f(col,row,view)$ with removed noise for at least some (one or more) of the different views and/or channels.

In one or more embodiments, after the prefiltered projection data $P_f$ has been generated, the reconstruction component 314 can generate or reconstruct a CT image using the prefiltered projection data $P_f$. This reconstructed image has a reduced level of streaks due to the reduced noise in the projection data, yet some blurring or reduction in resolution. This reconstructed image is generated from $P_f$ is thus referred to herein as the "streak free" image or $I_s$. This reconstructed image $I_s$ corresponds to the second image described in process 200. The reconstruction component 314 can also reconstruct another CT image using the original projection data P (the unfiltered projection data). This reconstructed image corresponds to the first image in process 200 and is referred to herein as image I. Alternatively, the original CT image I may be included in the original CT image data 306.

The fusion component 316 can further perform an image blending or fusion of image $I_s$ image I to generate a new, fused image (e.g., the fused CT image data 328) that contains subsets of pixels from each of the two images. In particular, the fusion component 316 can identify and extract first subset of pixels from image I corresponding to one or more non-uniform areas in the first image I and second subset of pixels corresponding to one or more uniform areas in streak free image $I_s$. The fusion component 316 can further generate the new, fused image by fusing the first subset of pixels with the second subset of pixels. In one or more embodiments, to facilitate this end, the fusion component 316 can identify the first subset of pixels and the second subset of pixels based on the noise level measures determined for each of the pixels in the streak free image $I_s$ and one or more defined threshold values for the noise level measures of the second subset. In particular, the fusion component 316 can compute the standard deviation (STD) for each pixel in the streak free image $I_s$. The fusion component 316 can further compute a histogram of the STD values and use the bin value with the maximum number of pixels as the noise level (NL). The fusion component can further generate the new fused image (newimg(i,j)) based on the STD values, the noise levels NL and a defined scaling factor sf in accordance with Equation 9.

Equation 9

$$newimg(i, j) = \begin{cases} I(i, j) & \text{if } STD(i, j) > sf * NL \\ I_s(i, j) & \text{if } STD(i, j) \leq NL \\ r * I(i, j) + (1 - r) * I_s(i, j) & r = \frac{STD(i, j) - NL}{(sf - 1)NL} \text{ otherwise} \end{cases}$$

In this regard, the fusion component 316 can compute the local STD for each pixel in the streak free image $I_s$ and calculate the noise level for the whole image $I_s$ based on the histogram. For most CT images there is a lot of uniform area, so the peak of the STD histogram will be the high noise level values associated with non-uniform areas, such vessels and bones (which will most often be a smaller representation of the entire image), and the noise levels in the uniform areas will be comparatively low. In accordance with Equation 9, if the local STD of a pixel is larger than the scaling factor sf, this indicates the pixel is associated with a non-uniform area, and the fusion component 316 can extract the corresponding pixel from the original image I. Likewise, if the local STD of a pixel is smaller than the scaling factor sf, this indicates the pixel is associated with a uniform area, and the fusion component 316 can extract the corresponding pixel from the original image $I_s$. In some embodiments, (and as defined by Equation 9), if the local STD of a pixel is near scaling factor sf or withing a defined range of the scaling factor sf (e.g., indicating the pixel is near or included in a partially uniform area and a partially non-uniform area), the fusion component 316 can combine perform a linear combination of the associated pixels from both images. The new fused image will be the final output image and be substantially streak free and sharp. In accordance with system 300, new, fused images generated by the fusion component 316 are represented by the fused CT image data 328.

Figure 4:
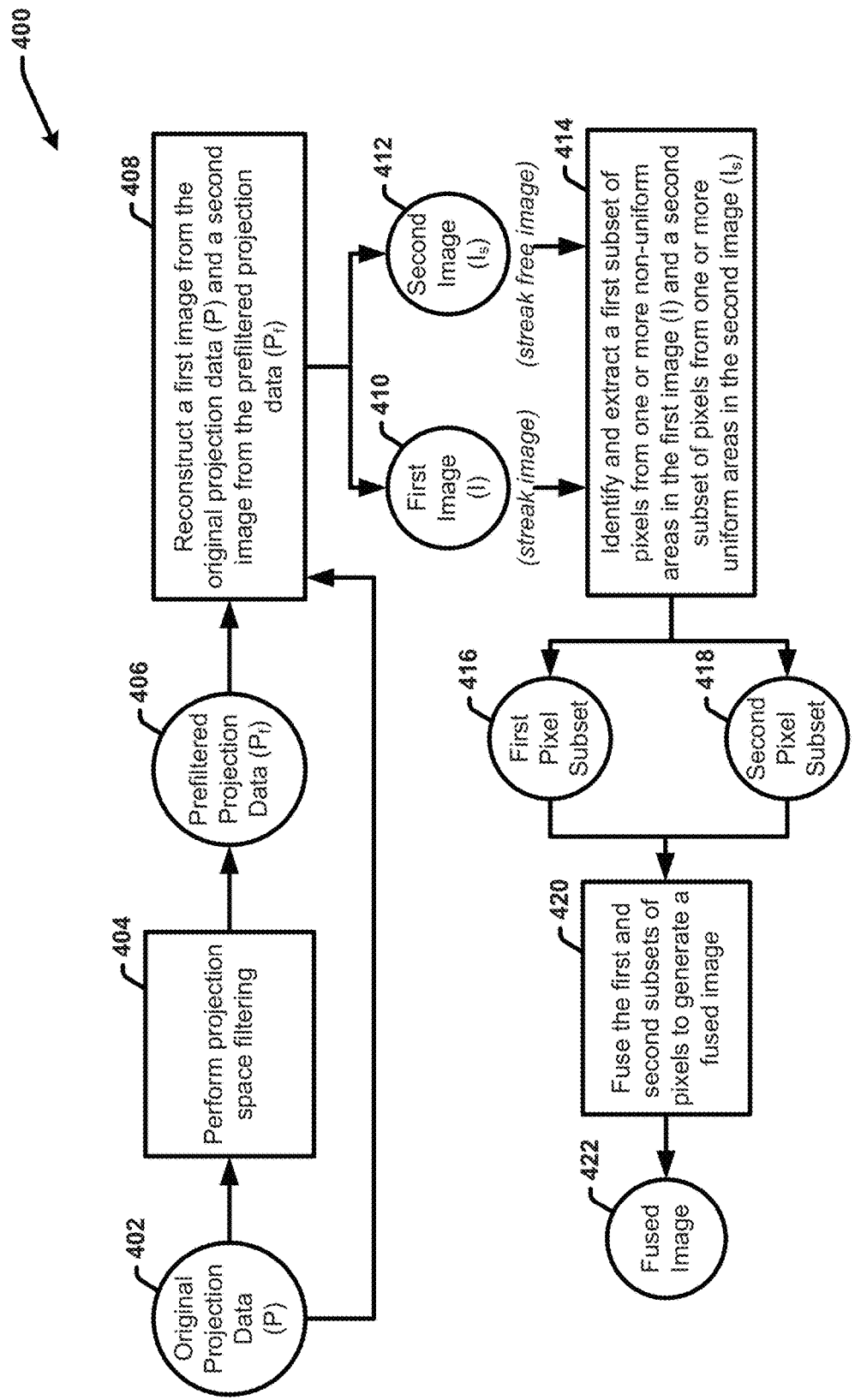
FIG. 4 presents a flow diagram of an example computer-implemented process for reducing streaks in a CT image in accordance with one or more embodiments of the disclosed subject matter.

FIG. 4 presents a flow diagram of an example computer-implemented process 400 for reducing streaks in a CT image in accordance with one or more embodiments of the disclosed subject matter. Process 400 corresponds to an example process that may be performed by the image data processing component 310 of system 300 using the projection space filtering process described above. Repetitive description of like elements employed in respective embodiments is omitted for sake of brevity.

With reference to FIGS. 3 and 4, in accordance with process, the projection filtering component 312 obtains original projection data 402 (P) and performs the projection space filtering processes at 404 to filter the original projection data 404 into prefiltered projection data ($P_f$) 406. For example, the original projection data (P) can be included in the original CT image data 306 and comprise a raw (e.g., unfiltered) set of projection CT data corresponding to a single 2D CT image. As described above, the projection space filtering process comprises estimating the pathlengths for each of the projections (p), determining the noise levels associated with each of the projections based on the estimated pathlengths or a combination of the pathlengths and the tube current mA values associated with each of the projections (e.g., using a predefined look-up table generated using the phantom study as described above), and filtering the projections to remove noise using a filter value/strength that increases relative to the noise levels.

At 408, the reconstruction component 314 can reconstruct a first CT image 410 (e.g., the streak image I) from the original projection data P and a second CT image 412 (e.g., the streak free image $I_s$) from the prefiltered projection data ($P_f$). At 414, the fusion component 316 can identify and extract a first subset of pixels 416 from one or more non-uniform areas in the first CT image 410 and a second subset of pixels 418 from one or more uniform areas in the second CT image 412. At 420, the fusion component can fuse the first and second subset of pixels to generate a fused CT image 422.

Process 400 requires the projection space filtering component 312 to have access to the original projection data (P) 402 acquired from a CT scan. In some implementations, this original projection data may not be available. For example, in some implementation, the system 300 may only have access to original CT images previously reconstructed using a standard or conventional CT image reconstruction processes. In some implementations of these embodiments when only original CT images are available, the image data processing component 310 can process the original CT image using a forward-projection processes (e.g., via projection component 320) to generate simulated or estimated projection data for the original CT image. Thereafter, the projection space filtering component 312 can perform the projection space filtering process on the simulated projection data to generate the streak free image $I_s$. In particular, the projection component 320 can forward project the pixels of the original CT image to estimate the projections p(col,row, view) for the different views and channels, and estimate the pathlengths for the simulated projections, as illustrated in FIG. 5.

Figure 5:
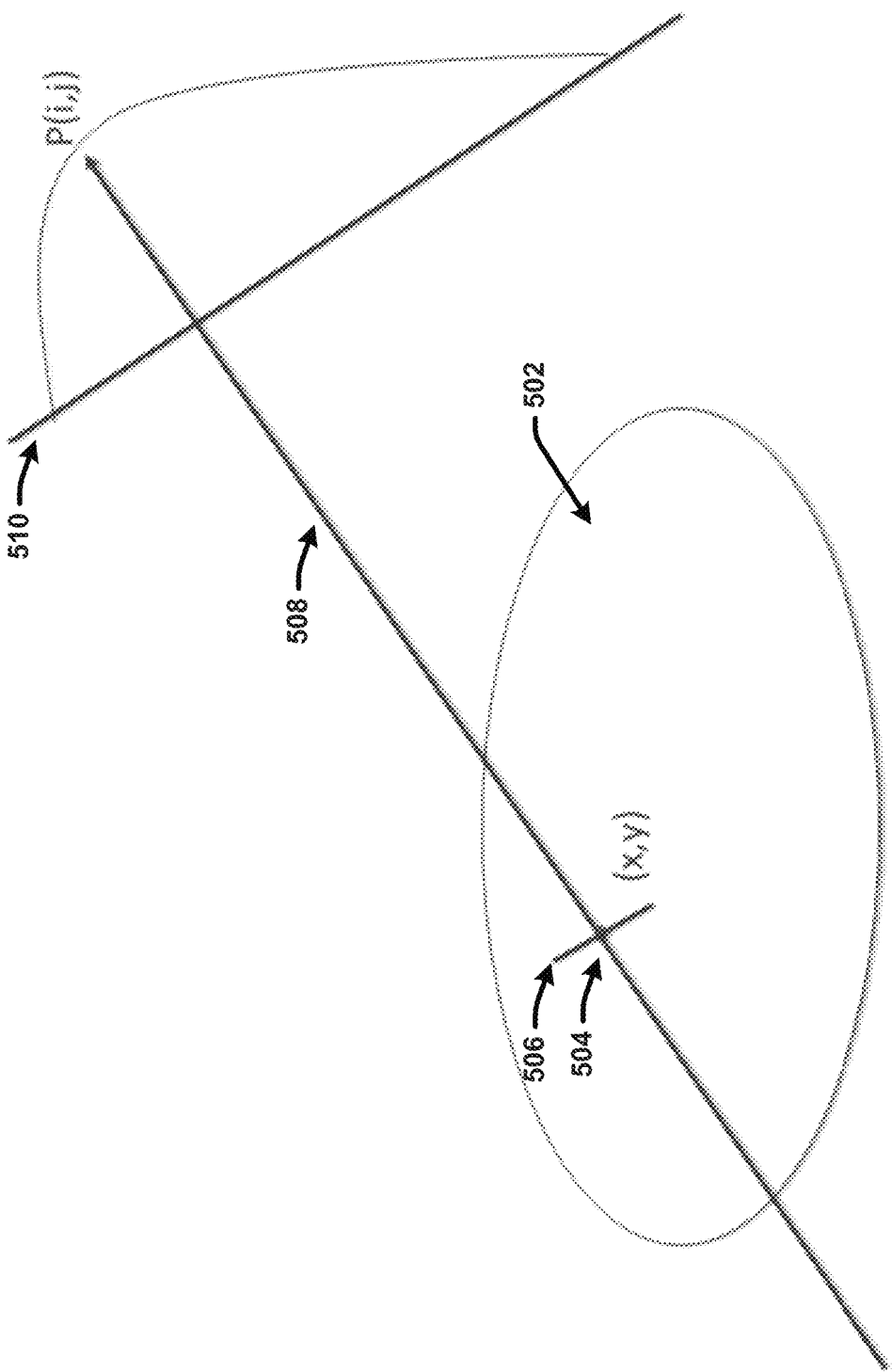
FIG. 5 illustrates forward projection of a CT image to obtain simulated projection data in accordance with one or more embodiments of the disclosed subject matter.

In this regard, FIG. 5 illustrates forward projection of a CT image to obtain simulated projection data in accordance with one or more embodiments of the disclosed subject matter. In FIG. 5, area 502 corresponds to the original CT image, point 504 corresponds to the 2D (x, y) coordinates of one pixel of the CT image, arrowed line 508 corresponds to the direction for a projection pass from (x,y) at a known view angle (j) and channel (i), and line 510 corresponds to a relative position of the detector array of the CT imaging system used to generate the original CT image. With reference to FIGS. 3 and 5, the projection component 320 can forward project the original CT image (i.e., the streak image I) for each pixel in the image and for each of the different view angles (n) to get simulated projections p(i,j),j∈[1 n] and i channel index. The forward projection means the integration of the pixel's CT value along arrowed line 508. In this regard, each of the pixels in an CT image have a CT value that denotes the attenuation level for that pixel, wherein the higher the CT value the higher the XR attenuation capability/capacity of that pixel. The integration of the CT value for the pixel corresponding to point 504 along arrowed line 508 can be used to calculate the XR attenuation along the line and used as the simulated projection value for its corresponding projection p, wherein the higher the integration value the longer pathlength. The pathlength can be determined as a function of the simulated projection value divided by the water attenuation coefficient (i.e., $p/\mu_w$). The noise for each of the simulated projections can also be estimated using the techniques described with reference to the projection space filtering process (e.g., using the look-up table).

Figure 6:
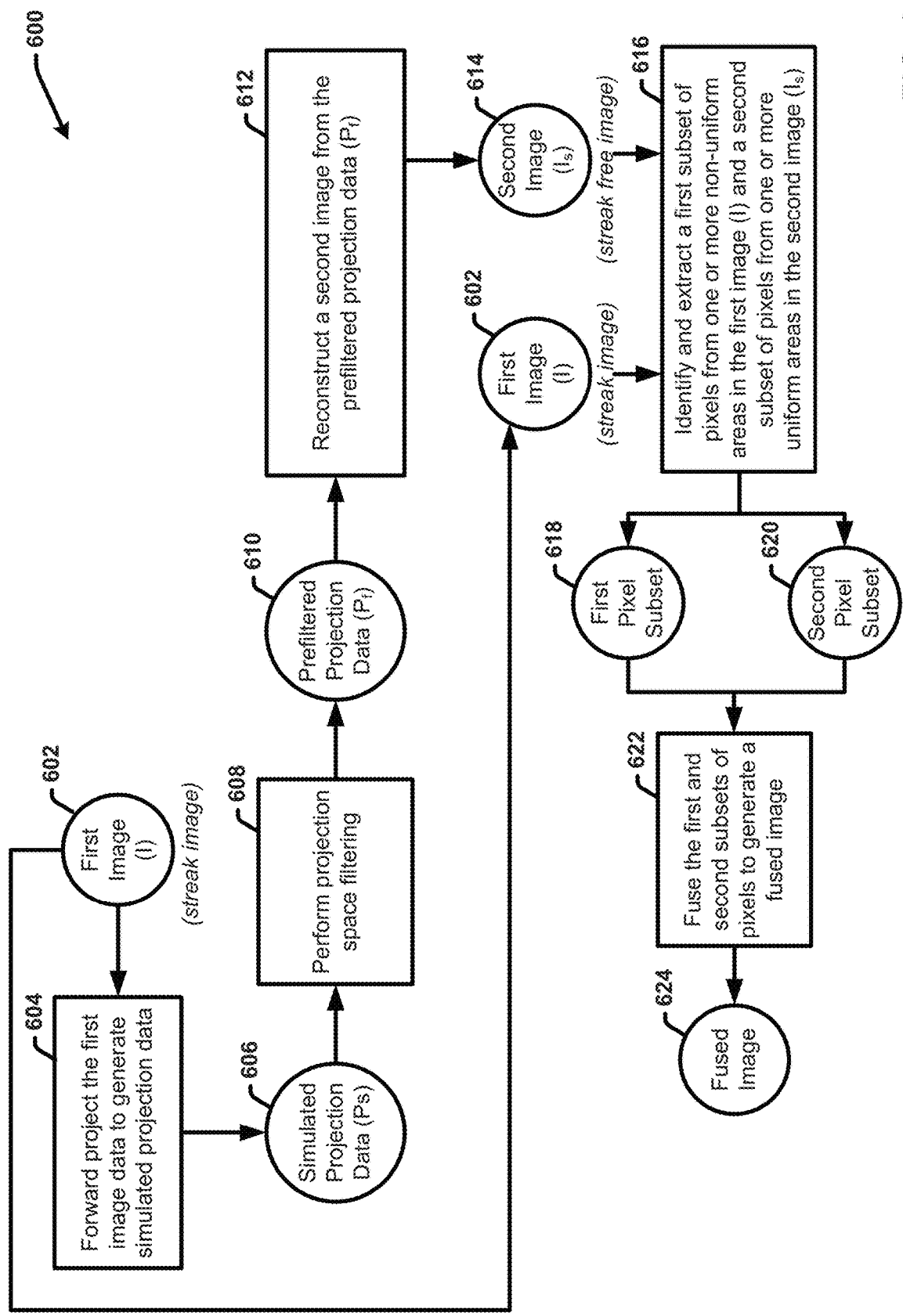
FIG. 6 presents a flow diagram of another example computer-implemented process for reducing streaks in a CT image in accordance with one or more embodiments of the disclosed subject matter.

FIG. 6 presents a flow diagram of another example computer-implemented process 600 for reducing streaks in a CT image in accordance with one or more embodiments of the disclosed subject matter. Process 600 is similar to process 400 yet incorporates forward projection of an original CT image to obtain simulated projection data from which the prefiltered projection data is generated. Repetitive description of like elements employed in respective embodiments is omitted for sake of brevity.

With reference to FIGS. 3 and 6, in accordance with process 600, at 604, the projection component can forward project a first CT image 602 (i.e., the streak image I) to generate simulated projection data (Ps) 606 (as illustrated in FIG. 5). At 608 the projection filtering component 312 can then perform the projection space filtering processes at 608 on the simulated projection data (Ps) 606 to filter the simulated projection data into prefiltered projection data ($P_f$) 610. At 612, the reconstruction component 314 can reconstruct a second CT image 614 (e.g., the streak free image $I_s$) from the prefiltered projection data ($P_f$). At 616, the fusion component 316 can identify and extract a first subset of pixels 618 from one or more non-uniform areas in the first CT image 602 and a second subset of pixels 620 from one or more uniform areas in the second CT image 614. At 622, the fusion component 316 can fuse the first and second subset of pixels to generate a fused CT image 624.

With reference again to FIGS. 3 and 5, in other embodiments when only original CT images are available and the original projection data P for the CT images is not available, the image data processing component 310 can process the original CT image using image space filtering (e.g., via mage space filtering component 318) to generate the streak free image $I_s$. With these embodiments, the projection component 320 can forward project the original CT image as illustrated in FIG. 5 to generate the simulated projections for the original CT image, the estimated pathlengths for the simulated projections and the noise levels for the simulated projections. For each pixel (x,y) in the original CT image (i.e., image I), the image space filtering component 518 can filter the respective pixels for each view (j). In this regard, with reference to FIG. 5, arrowed line 508 indicates the direction of for projection pass (x,y) at the view j. The image space filtering component 318 applies the filter along the direction perpendicular to the projection (i.e., perpendicular to line 506), and the convolution kernel K is determined based on the estimated noise level associated with each projection (e.g., in accordance with the techniques described with reference to the projection space filtering processes). In this regard, the image space filtering component 318 filters each pixel (x,y) for each view and summed together, divided by n (the number of view). With this method, the respective pixel (x,y) will be filtered stronger at the views with longer pathlengths and less (or not at all) for the view with shorter pathlengths. It will be filtered less or not filtered at view with short path length. After all pixels in the original CT image I are filtered, the resulting image becomes the streak free image $I_s$. Thereafter, the fusion component 316 can perform the image fusion/blending process using the original image I and the streak free image $I_s$ as described above.

Figure 7:
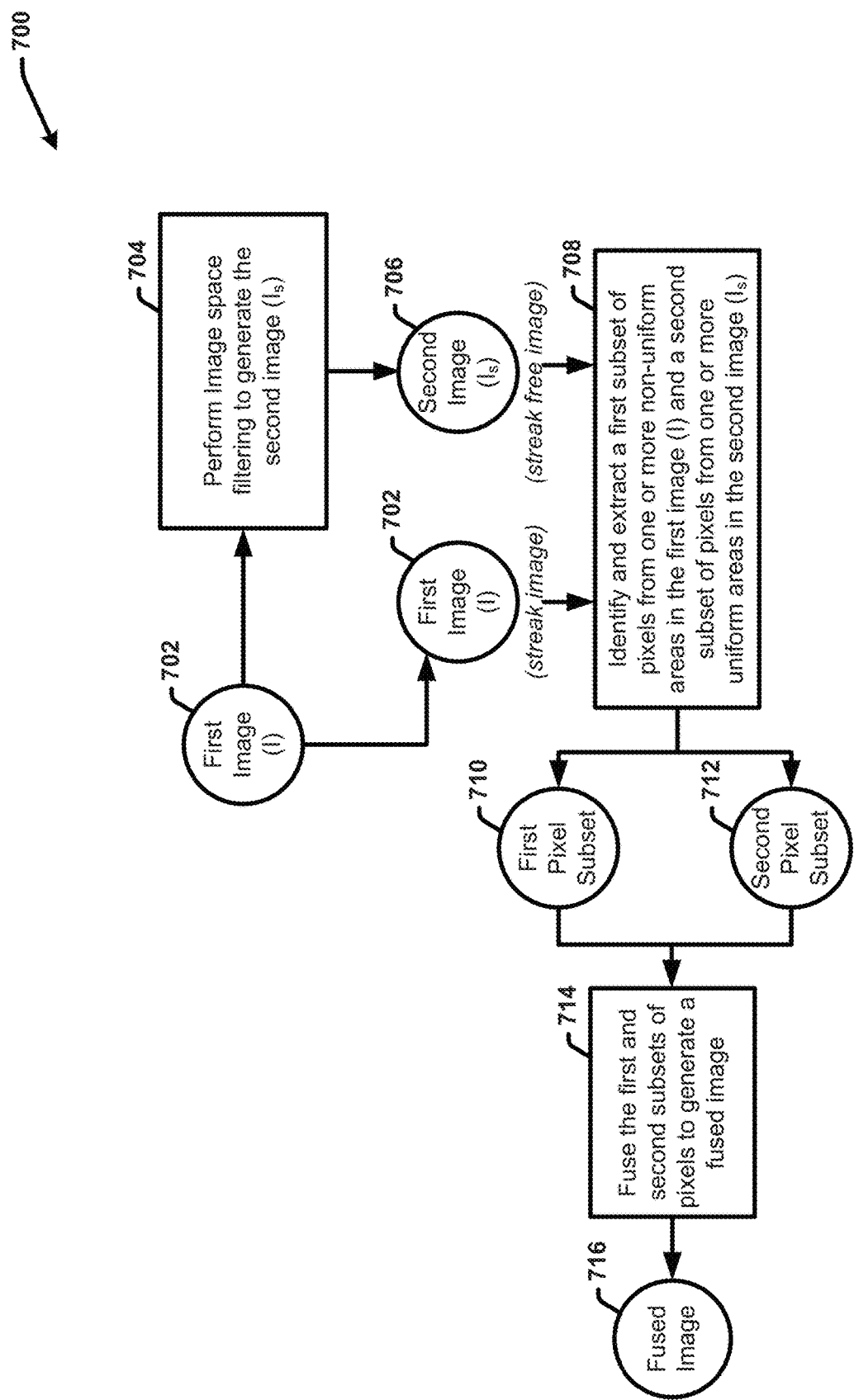
FIG. 7 presents a flow diagram of another example computer-implemented process for reducing streaks in a CT image in accordance with one or more embodiments of the disclosed subject matter.

FIG. 7 presents a flow diagram of another example computer-implemented process 700 for reducing streaks in a CT image in accordance with one or more embodiments of the disclosed subject matter. 700 is similar to processes 400 and 600 with the modification of usage of image space filtering to generating the streak free image $I_s$. Repetitive description of like elements employed in respective embodiments is omitted for sake of brevity.

With reference to FIGS. 3 and 7, in accordance with process 700, at 704, the image space filtering component 318 can perform image space filtering on a first CT image 702 (i.e., the streak image I) to generate the second CT image 706 (i.e., the streak free image $I_s$). At 708 the fusion component 316 can identify and extract a first subset of pixels 710 from one or more non-uniform areas in the first CT image 702 and a second subset of pixels 712 from one or more uniform areas in the second CT image 706. At 714, the fusion component 316 can fuse the first and second subset of pixels to generate a fused CT image 716.

Figure 8:
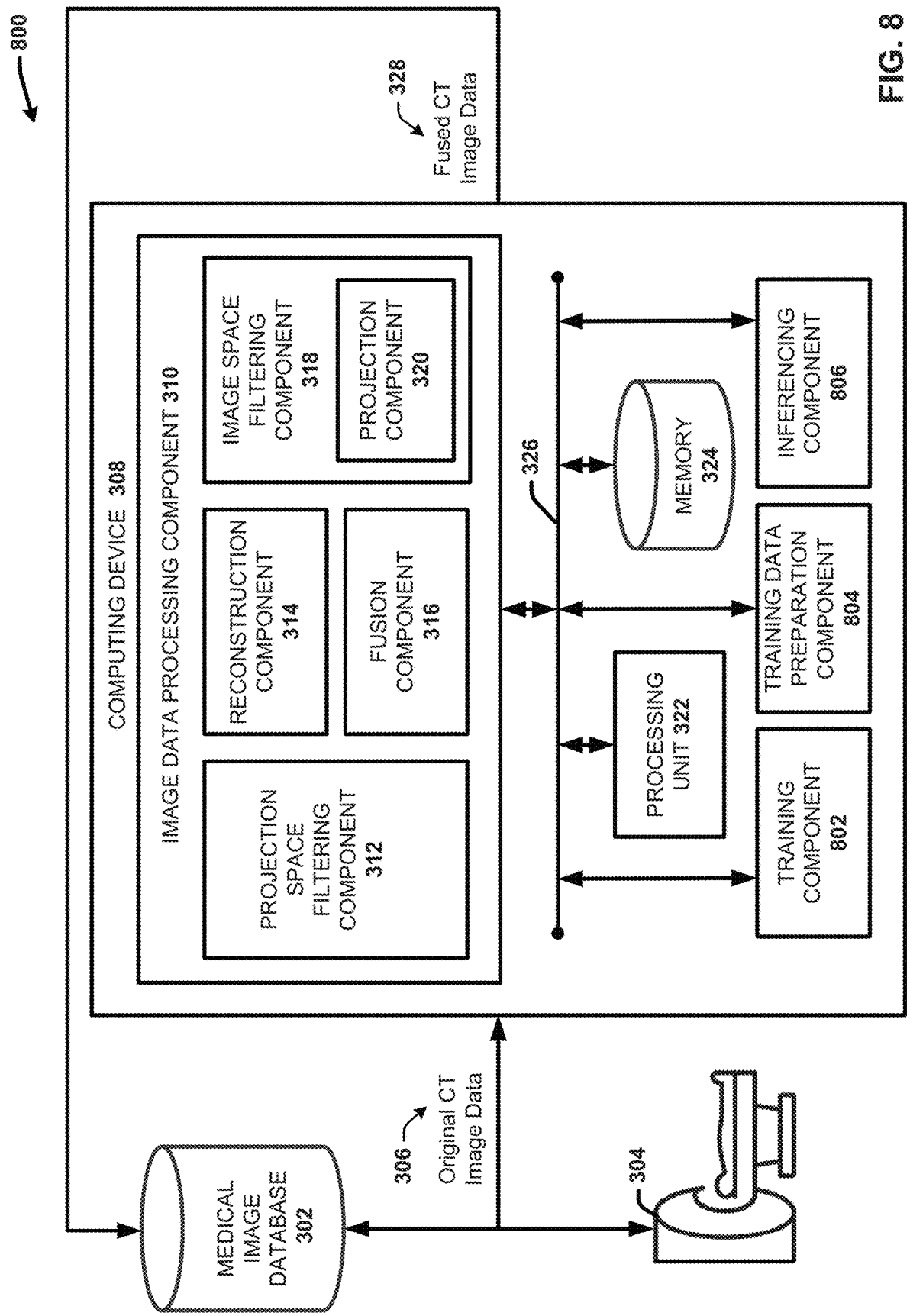
FIG. 8 presents another example computing system that facilitates reducing streaks in CT images in accordance with one or more embodiments of the disclosed subject matter.

FIG. 8 presents another example computing system 800 that facilitates reducing streaks in CT images in accordance with one or more embodiments of the disclosed subject matter. System 800 is similar to system 300 with the addition of training component 802, training data preparation component 804 and inferencing component 806 to the computing device 308. Repetitive description of like elements employed in respective embodiments is omitted for sake of brevity.

In accordance with system 800, the fused CT image data 328 generated using one or more of the techniques described above (e.g., process 200, process, 400, process 600 and/or process 700) can be added to the medical image database 302 (or another suitable database) and used to train and develop one or more image transformation models using machine learning techniques (e.g., via the training component 802) to automatically reduce streaks in a given input CT image. In this regard, one or more of the methods for generating fused images described above can also be used to prepare a training data set for training (e.g., via the training component 802) a deep neural network model to generate an optimized image corresponding to the fused image described above given an original CT image (e.g., processed using a standard reconstruction processes) as input.

For example, with reference to FIGS. 2 and 8, the training dataset can comprise pairs CT images, wherein each pair comprises an original CT image reconstructed using the standard reconstruction process corresponding to the first image in process 200, and a fused CT image corresponding to the third image in process 200. The process used to generate the third image in each pair can include process 400, process 600, process 700, or combinations thereof). In some embodiments, the training process can comprise training the neural network (e.g., via the training component 804) to transform the original CT images into corresponding versions of their paired fused images. For example, in some embodiments, the neural network can comprise a transformer network (an image transformation model) comprising an encoder network, a latent space, and a decoder network. The training component 802 can train the encoder network to encode the original CT image into a latent space representation thereof and train the decoder network to decode the latent space representation into the paired fused version of the original CT image. After the image transformation model has been trained. The inferencing component 806 can apply the trained image transformation model to a new CT image comprising streaks (e.g., a CT image include in the original CT image data 306), and the output of the image transformation model will comprise an optimized image with reduced streaks corresponding to fused CT image data 328.

Additionally, or alternatively, the training process can comprise training (e.g., via the training component 802) the neural network model to estimate streak data included in the original CT images, wherein the streak data used for the training process can be calculated based on difference between the original CT images and their paired fused images. With these embodiments, the training data preparation component 804 can generate the streak data for each pair of images in the training dataset based on differences between the original CT images and their paired fused images. With these embodiments, the output of the trained neural network comprises predicted streak data for a given original CT image. After the network has been trained, the trained neural network, the inferencing component 806 can applied the trained network to a new original CT image (e.g., with streaks) to generate estimated streak data for the new CT image. The inferencing component 806 can further generate a final optimized CT image with reduced streaks by removing the estimated streak data (output by the neural network model) from the original CT image.

Figure 9:
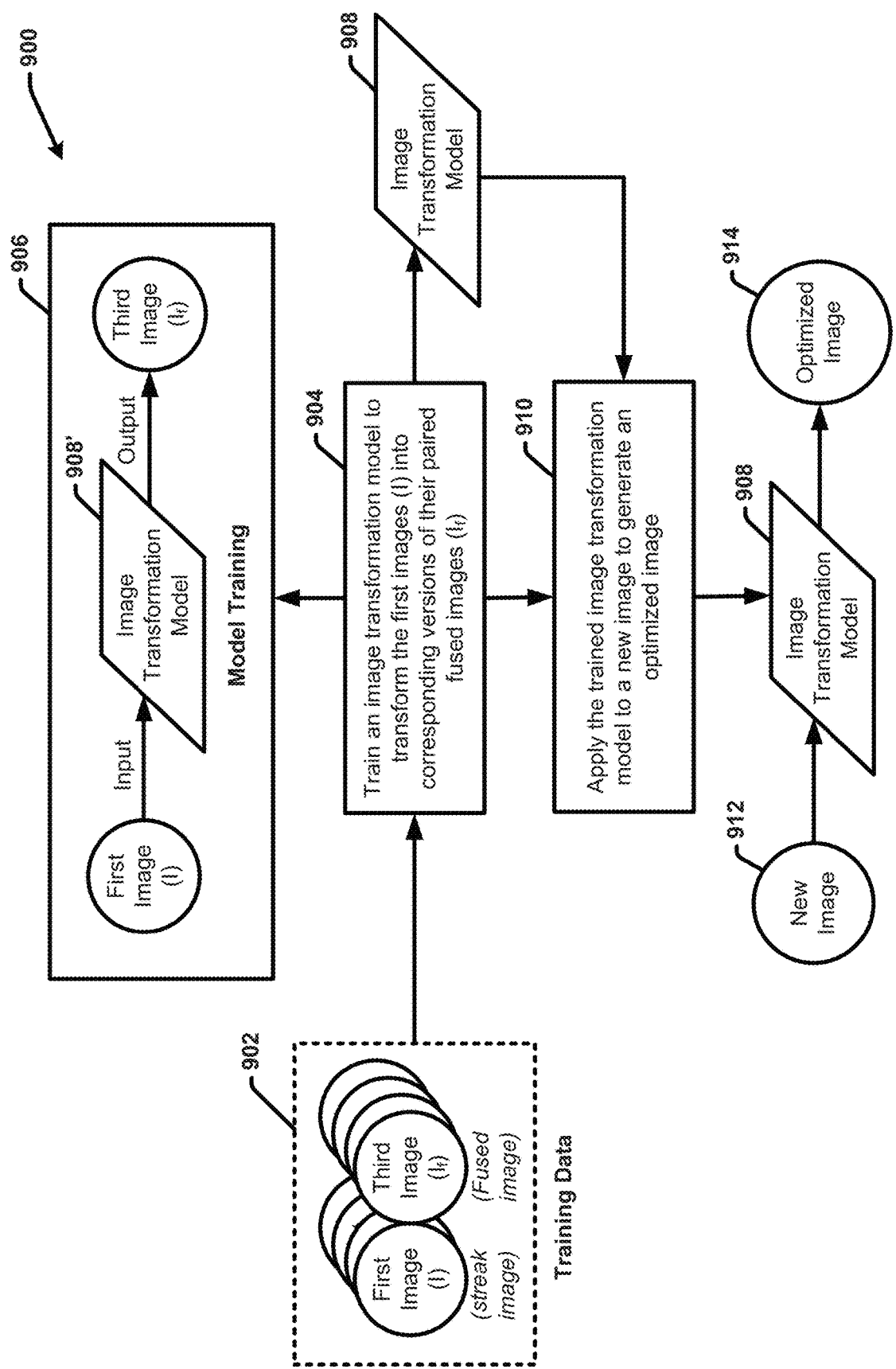
FIG. 9 presents a flow diagram of an example computer-implemented process for reducing streaks in CT images using machine learning techniques in accordance with one or more embodiments of the disclosed subject matter.

FIG. 9 presents a flow diagram of an example computer-implemented process 900 for reducing streaks in CT images using machine learning techniques in accordance with one or more embodiments of the disclosed subject matter. Process 900 corresponds to an end-to-end process that can be performed by system 800 using the training component 804, and the inferencing component 808. Repetitive description of like elements employed in respective embodiments is omitted for sake of brevity.

Process 900 involves a model training phase 906 in which an image transformation model 908' is trained (e.g., via training component 802) on the training dataset 902. As noted above, the training dataset 902 can comprise a plurality of pairs of images, wherein each image pair comprises a streak image corresponding to the first image in process 200 and a fused image (If) corresponding to the third image in process 200. In this regard, at 904, the training component 802 can train the image transformation model 908' to transform the first images into their paired third images (the fused images) using one or more machine learning techniques (e.g., supervised training, unsupervised training, semi-supervised training, and the like). The type of the image transformation model 908' can vary. For example, the image transformation model 908' can comprises one or more deep learning models, one or more neural network models, deep neural network models (DNNs), one or more convolutional neural network models (CNNs), one or more generative adversarial neural network models (GANs), one or more long short-term memory models (LSTMs), one or more attention-based models, one or more transformers, and the like. The image transformation model 908' is denoted with an asterisk ' to indicate the model is not yet trained and/or undergoing the model training phase and without an asterisk ' to indicate the model has completed training. In this regard, the output of the training phase includes a trained version of the image transformation model 908. At 910, the inferencing component can apply the trained image transformation model 908 to a new CT image 912 to generate an optimized CT image 914 that has a reduced level of streaks compared to the new image 912.

Figure 10:
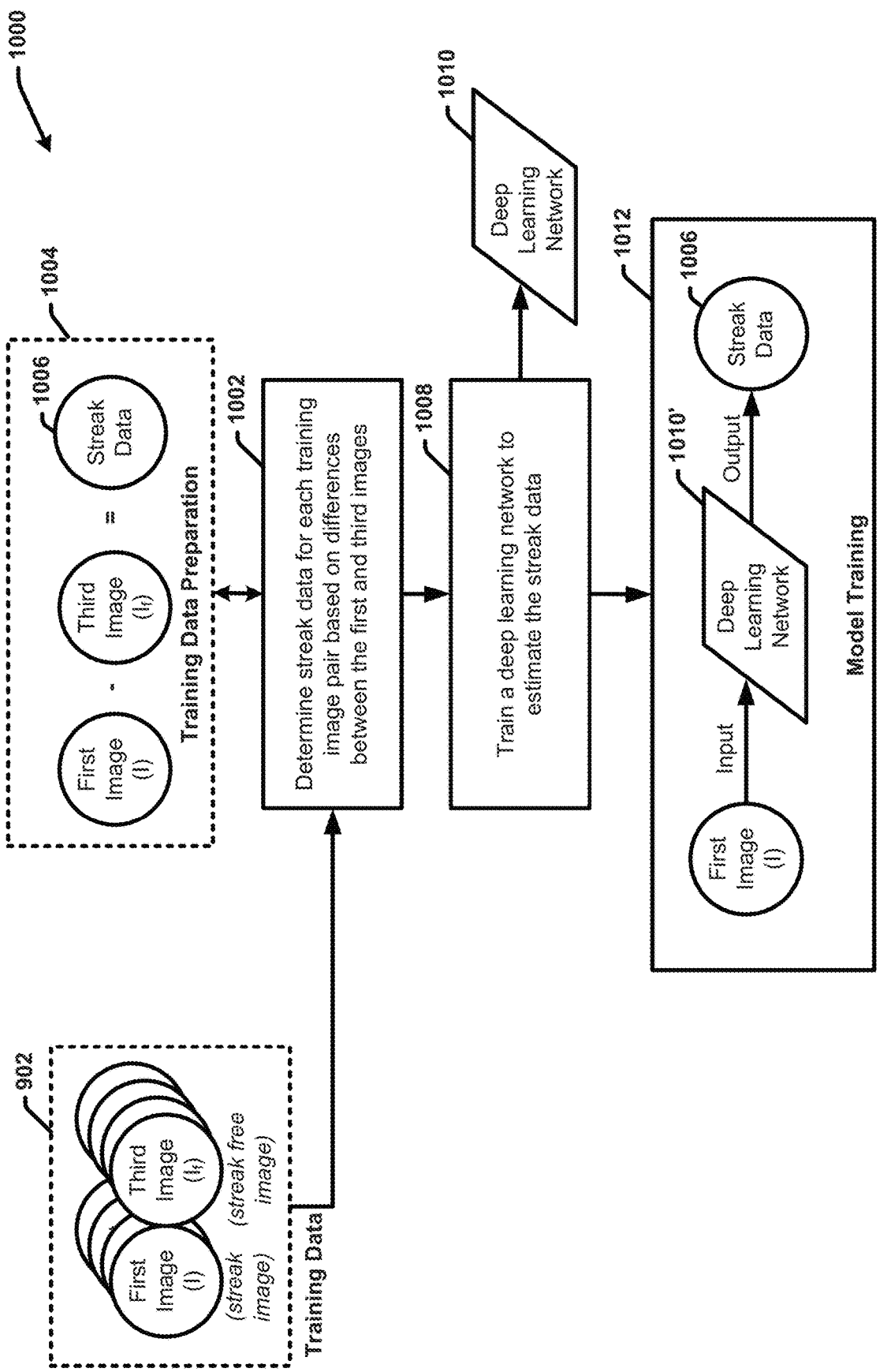
FIG. 10 presents a flow diagram of another example computer-implemented process for reducing streaks in CT images using machine learning techniques in accordance with one or more embodiments of the disclosed subject matter.

FIG. 10 presents a flow diagram of another example computer-implemented process 1000 for reducing streaks in CT images using machine learning techniques in accordance with one or more embodiments of the disclosed subject matter. Process 1000 corresponds to another ML model training process that can be performed by the training component 802 and the training data preparation component 804 of system 800. Repetitive description of like element employed in respective embodiments is omitted for sake of brevity.

Process 1000 involves a training data preparation phase 1004 and a model training phase 1012. In accordance with the training data preparation phase 1004, at 1002 the training data preparation component 804 can process the training data 902 to determine streak data 1006 for each training image pair. The streak data 1006 corresponds to the streak image data removed from the first images. In various embodiments, the training data preparation component 804 can determine/generate the streak data for each pair based on differences between the first images and the third images (e.g., the first image I minus the third image $I_f$).

At 1008, the training component 802 can then perform the training phase 1012 and train a deep learning network 1010' to estimate the streak data 1006 for the respective first images. In this regard, the input to the deep learning network 1010' comprises the first image and the output comprises the estimated streak data 1006. The deep learning network 1010' is denoted with an asterisk ' to indicate the model is not yet trained and/or undergoing the model training phase and without an asterisk ' to indicate the model has completed training. In this regard, the output of the training phase 1012 includes a trained version of the deep learning network 1010 configured to receive an original CT image as input and estimate the steak data included in that image.

Figure 11:
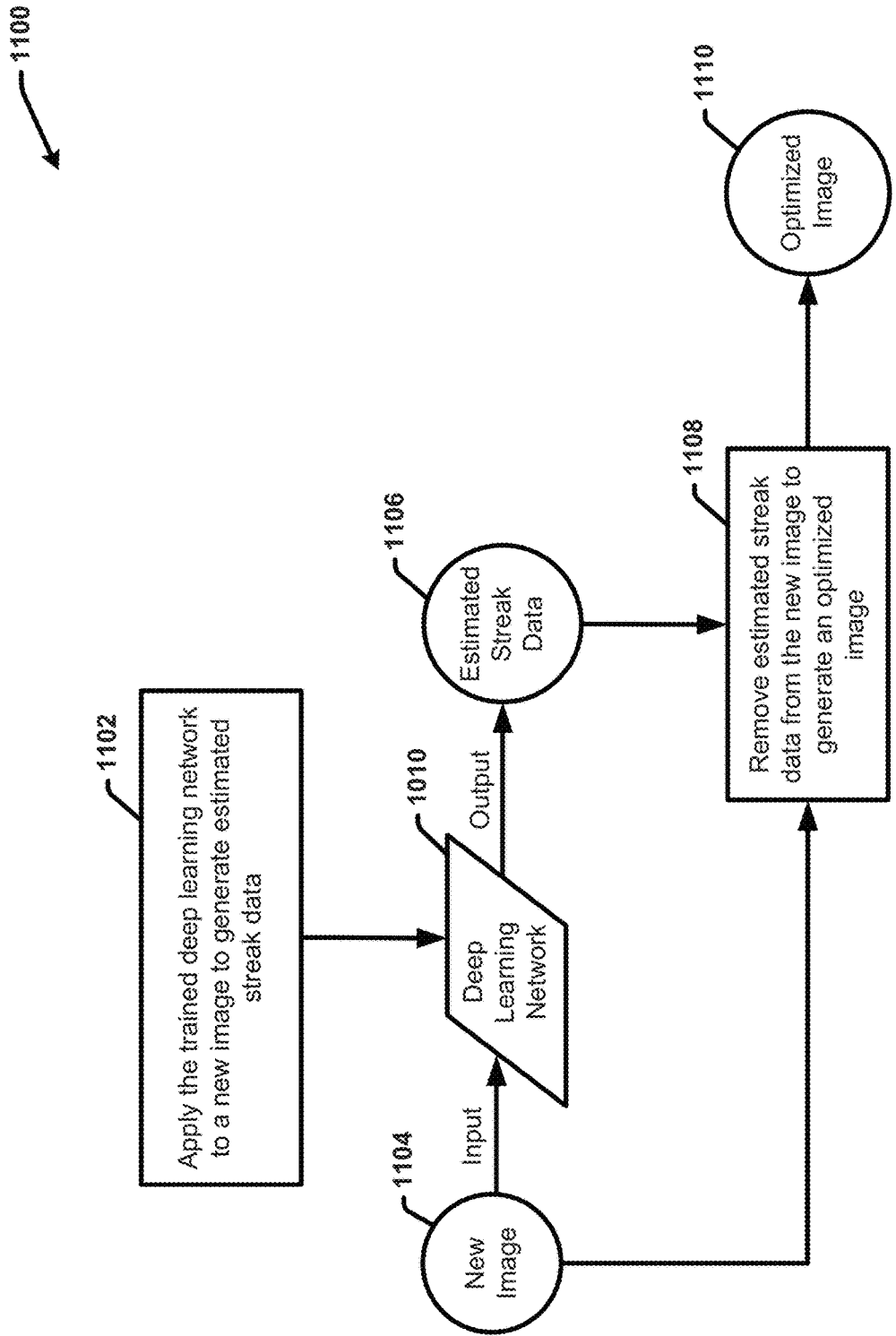
FIG. 11 presents a flow diagram of another example computer-implemented process for reducing streaks in CT images using machine learning techniques in accordance with one or more embodiments of the disclosed subject matter.

FIG. 11 presents a flow diagram of another example computer-implemented process 1100 for reducing streaks in CT images using machine learning techniques in accordance with one or more embodiments of the disclosed subject matter. Process 1100 corresponds to an inferencing phase or model application phase that can be performed by the inferencing component 806 using the trained version of the deep learning network 1010. In accordance with process 1100, at 1102, the inferencing component 806 can apply the trained deep learning network 1010 to a new CT image 1104 to generate estimated streak data 1106 for the new CT image 1104. At 1108, the inferencing component 806 can remove the estimate streak data from the new CT image 1104 to generate an optimized CT image 1110 that has a reduced level of streaks compared to the new image 1104.

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, procedural programming languages, such as the "C" programming language or similar programming languages, and machine-learning programming languages such as like CUDA, Python, Tensorflow, PyTorch, and the like. The computer readable program instructions can execute entirely on the user's computer, partly on the user's computer, as a stand-alone software package, partly on the user's computer and partly on a remote computer or entirely on the remote computer or server using suitable processing hardware. In the latter scenario, the remote computer can be connected to the user's computer through any type of network, including a local area network (LAN) or a wide area network (WAN), or the connection can be made to an external computer (for example, through the Internet using an Internet Service Provider). In various embodiments involving machine-learning programming instructions, the processing hardware can include one or more graphics processing units (GPUs), central processing units (CPUs), and the like. For example, one or more of the disclosed machine-learning models (e.g., the image transformation model 908, the deep learning network 1010 and/or combinations thereof) may be written in a suitable machine-learning programming language and executed via one or more GPUs, CPUs or combinations thereof. In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 12, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 12:
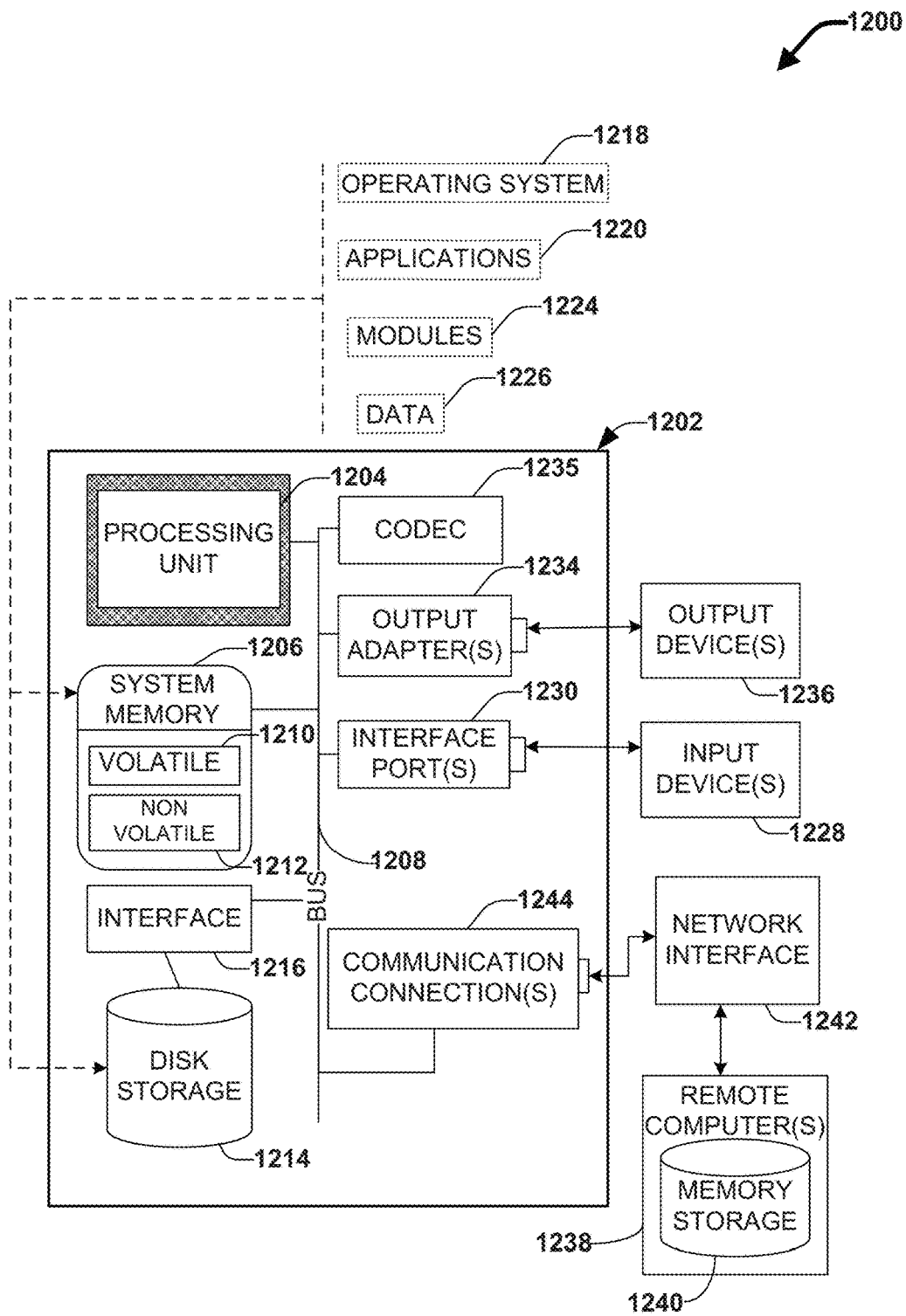
FIG. 12 illustrates a block diagram of an example, non-limiting operating environment in which one or more embodiments described herein can be facilitated.

With reference to FIG. 12, an example environment 1200 for implementing various aspects of the claimed subject matter includes a computer 1202. The computer 1202 includes a processing unit 1204, a system memory 1206, a codec 1235, and a system bus 1208. The system bus 1208 couples system components including, but not limited to, the system memory 1206 to the processing unit 1204. The processing unit 1204 can be any of various available processors. Dual microprocessors, one or more GPUs, CPUs, and other multiprocessor architectures also can be employed as the processing unit 1204.

The system bus 1208 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1206 includes volatile memory 1210 and non-volatile memory 1212, which can employ one or more of the disclosed memory architectures, in various embodiments. The basic input/output system (BIOS), containing the basic routines to transfer information between elements within the computer 1202, such as during start-up, is stored in non-volatile memory 1212. In addition, according to present innovations, codec 1235 can include at least one of an encoder or decoder, wherein the at least one of an encoder or decoder can consist of hardware, software, or a combination of hardware and software. Although, codec 1235 is depicted as a separate component, codec 1235 can be contained within non-volatile memory 1212. By way of illustration, and not limitation, non-volatile memory 1212 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1212 can employ one or more of the disclosed memory devices, in at least some embodiments. Moreover, non-volatile memory 1212 can be computer memory (e.g., physically integrated with computer 1202 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1210 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1202 can also include removable/non-removable, volatile/non-volatile computer storage medium. FIG. 12 illustrates, for example, disk storage 1214. Disk storage 1214 includes, but is not limited to, devices like a magnetic disk drive, solid state disk (SSD), flash memory card, or memory stick. In addition, disk storage 1214 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1214 to the system bus 1208, a removable or non-removable interface is typically used, such as interface 1216. It is appreciated that disk storage 1214 can store information related to a user. Such information might be stored at or provided to a server or to an application running on a user device. In one embodiment, the user can be notified (e.g., by way of output device(s) 1236) of the types of information that are stored to disk storage 1214 or transmitted to the server or application. The user can be provided the opportunity to opt-in or opt-out of having such information collected or shared with the server or application (e.g., by way of input from input device(s) 1228).

It is to be appreciated that FIG. 12 describes software that acts as an intermediary between users and the basic computer resources described in the suitable operating environment 1200. Such software includes an operating system 1218. Operating system 1218, which can be stored on disk storage 1214, acts to control and allocate resources of the computer 1202. Applications 1220 take advantage of the management of resources by operating system 1218 through program modules 1224, and program data 1226, such as the boot/shutdown transaction table and the like, stored either in system memory 1206 or on disk storage 1214. It is to be appreciated that the claimed subject matter can be implemented with various operating systems or combinations of operating systems.

A user enters commands or information into the computer 1202 through input device(s) 1228. Input devices 1228 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1204 through the system bus 1208 via interface port(s) 1230. Interface port(s) 1230 include, for example, a serial port, a parallel port, a game port, and a universal serial bus (USB). Output device(s) 1236 use some of the same type of ports as input device(s) 1228. Thus, for example, a USB port can be used to provide input to computer 1202 and to output information from computer 1202 to an output device 1236. Output adapter 1234 is provided to illustrate that there are some output devices 1236 like monitors, speakers, and printers, among other output devices 1236, which require special adapters. The output adapters 1234 include, by way of illustration and not limitation, video and sound cards that provide a means of connection between the output device 1236 and the system bus 1208. It should be noted that other devices or systems of devices provide both input and output capabilities such as remote computer(s) 1238.

Computer 1202 can operate in a networked environment using logical connections to one or more remote computers, such as remote computer(s) 1238. The remote computer(s) 1238 can be a personal computer, a server, a router, a network PC, a workstation, a microprocessor based appliance, a peer device, a smart phone, a tablet, or other network node, and typically includes many of the elements described relative to computer 1202. For purposes of brevity, only a memory storage device 1240 is illustrated with remote computer(s) 1238. Remote computer(s) 1238 is logically connected to computer 1202 through a network interface 1242 and then connected via communication connection(s) 1244. Network interface 1242 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1244 refers to the hardware/software employed to connect the network interface 1242 to the bus 1208. While communication connection 1244 is shown for illustrative clarity inside computer 1202, it can also be external to computer 1202. The hardware/software necessary for connection to the network interface 1242 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor that executes the computer executable components stored in the memory, wherein the computer executable components comprise:
   an image processing component that obtains a pair of computed tomography images reconstructed from a same set of projection data, the pair comprising a first image reconstructed from the projection data using a standard reconstruction process and a second image reconstructed from the projection data using a filtering reconstruction process that results in the second image comprising a first reduced level of streaks relative to the first image; and
   a fusion component that generates a third image by fusing a first subset of pixels extracted from one or more non-uniform areas in the first image and a second subset of pixels extracted from one or more uniform areas in the second image, wherein the third image comprises a second reduced level of streaks relative to the first image.

2. The system of claim 1, wherein the fusion component determines noise level measures for each pixel of the second image and identifies the first subset of pixels and the second subset of pixels based on the noise level measures and one or more defined threshold values for the noise level measures of the second subset.

3. The system of claim 1, wherein the standard reconstruction process comprises reconstructing the first image from the projection data without prefiltering the projection data and wherein the filtering reconstruction process comprises filtering the projection data into prefiltered projection data and reconstructing the second image from the prefiltered projection data, wherein the prefiltered projection data comprises projections with reduced noise as a function of pathlengths of the projections or a function of a combination of the pathlengths and tube current, and wherein an amount of the reduced noise increases as the pathlengths increase or the tube current decreases.

4. The system of claim 3, wherein the computer executable components further comprise:
   a projection component that estimates the projection data from the first image using a forward image projection process, resulting in simulated projection data, and wherein the filtering reconstruction process comprises filtering the simulated projection into the prefiltered projection data as opposed to the filtering the projection data.

5. The system of claim 3, wherein the computer executable components further comprise:
   a projection space filtering component that generates the prefiltered projection data from the projection data, wherein the projection space filtering component estimates the pathlengths of the projections using a projection smoothing process, estimates noise levels of the projections based on the pathlengths or a combination of the pathlengths and tube current, and determines the amount of the reduced noise for the projections based on the noise levels.

6. The system of claim 5, wherein the computer executable components further comprise:
   a reconstruction component that generates the second image from the prefiltered projection data.

7. The system of claim 1, wherein the computer executable components further comprise:
   a training component that receives a plurality of pairs of computed tomography images respectively comprising original images generated using the standard reconstruction process and fused images corresponding to the third image generated by the fusion component and trains an image transformation model comprising a neural network to transform the original images into corresponding versions of the fused images, resulting in a trained image transformation model.

8. The system of claim 7, wherein the computer executable components further comprise:
   an inferencing component that receives a new computed tomography image reconstructed from a new set of projection data using the standard reconstruction process and generates an optimized image with a reduced level of streaks relative to the new computed tomography images using the trained image transformation model.

9. The system of claim 7, wherein the computer executable components further comprise:

a training data preparation component that determines streak data for each pair of the plurality of pairs based on differences between the original images and the fused images, and wherein the training component trains the neural network to estimate the streak data given the original images as input, resulting in estimated streak data, and wherein the image transformation model removes the estimated streak data from the original images to generate the corresponding versions of the fused images.

10. The system of claim 1, wherein the filtering reconstruction process comprises an image space filtering process and wherein the computer executable components further comprise:
an image space filtering component that performs the image space filtering process on the first image to generate the second image.

11. A method, comprising:
obtaining, by a system comprising a processor, a pair of computed tomography images reconstructed from a same set of projection data, the pair comprising a first image reconstructed from the projection data using a standard reconstruction process and a second image reconstructed from the projection data using a filtering reconstruction process that results in the second image comprising a first reduced level of streaks relative to the first image; and
generating, by the system, a third image by fusing a first subset of pixels extracted from one or more non-uniform areas in the first image and a second subset of pixels extracted from one or more uniform areas in the second image, wherein the third image comprises a second reduced level of streaks relative to the first image.

12. The method of claim 11, further comprising:
determining, by the system, noise level measures for each pixel of the second image; and
identifying, by the system, the first subset of pixels and the second subset of pixels based on the noise level measures and one or more defined threshold values for the noise level measures of the second subset.

13. The method of claim 11, wherein the standard reconstruction process comprises reconstructing the first image from the projection data without prefiltering the projection data and wherein the filtering reconstruction process comprises filtering the projection data into prefiltered projection data and reconstructing the second image from the prefiltered projection data, wherein the prefiltered projection data comprises projections with reduced noise as a function of pathlengths of the projections or a function of a combination of the pathlengths and tube current, and wherein an amount of the reduced noise increases as the pathlengths increase or the tube current decreases.

14. The method of claim 13, further comprising:
estimating, by the system, the projection data from the first image using a forward image projection process, resulting in simulated projection data, and wherein the filtering reconstruction process comprises filtering the simulated projection into the prefiltered projection data as opposed to the filtering the projection data.

15. The method of claim 13, further comprising performing the prefiltering projection process by the system, comprising:
estimating, by the system, the pathlengths of the projections using a projection smoothing process;
estimating, by the system, noise levels of the projections based on the pathlengths or a combination of the pathlengths and tube current;
determining, by the system, the amount of the reduced noise for the projections based on the noise levels; and
generating, by the system, the prefiltered projection data from the projection data by removing the amount of the reduced noise from the projections.

16. The method of claim 15, further comprising:
generating, by the system, the second image from the prefiltered projection data.

17. The method of claim 11, further comprising:
receiving, by the system, a plurality of pairs of computed tomography images respectively comprising original images generated using the standard reconstruction process and fused images corresponding to the third image; and
training, by the system, an image transformation model comprising a neural network to transform the original images into corresponding versions of the fused images, resulting in a trained image transformation model.

18. The method of claim 17, further comprising:
receiving, by the system, a new computed tomography image reconstructed from a new set of projection data using the standard reconstruction process; and
generating, by the system, an optimized image with a reduced level of streaks relative to the new computed tomography images using the trained image transformation model.

19. The system of claim 17, further comprising:
determining, by the system, streak data for each pair of the plurality of pairs based on differences between the original images and the fused images, and wherein the training comprises training the neural network to estimate the streak data given the original images as input, resulting in estimated streak data, and wherein the image transformation model removes the estimated streak data from the original images to generate the corresponding versions of the fused images.

20. The method of claim 11, wherein the filtering reconstruction process comprises an image space filtering process and wherein the method further comprises:
performing, by the system, the image space filtering process on the first image to generate the second image.

21. A non-transitory machine-readable storage medium, comprising executable instructions that, when executed by a processor, facilitate performance of operations, comprising:
obtaining a pair of computed tomography images reconstructed from a same set of projection data, the pair comprising a first image reconstructed from the projection data using a standard reconstruction process and a second image reconstructed from the projection data using a filtering reconstruction process that results in the second image comprising a first reduced level of streaks relative to the first image; and
generating a third image by fusing a first subset of pixels extracted from one or more non-uniform areas in the first image and a second subset of pixels extracted from one or more uniform areas in the second image, wherein the third image comprises a second reduced level of streaks relative to the first image.

22. The non-transitory machine-readable storage medium of claim 21, wherein the operations further comprise:
determining noise level measures for each pixel of the second image; and identifying the first subset of pixels and the second subset of pixels based on the noise level measures and one or more defined threshold values for the noise level measures of the second subset.

* * * * *